(12) United States Patent
Luengo et al.

(10) Patent No.: US 6,545,031 B1
(45) Date of Patent: Apr. 8, 2003

(54) ENDOTHELIN RECEPTOR ANTAGONISTS

(75) Inventors: Juan Ignacio Luengo, Audubon, PA (US); John Duncan Elliott, Wayne, PA (US); Jia-Ning Xiang, Wayne, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/699,951

(22) Filed: Oct. 30, 2000

Related U.S. Application Data

(63) Continuation of application No. 09/249,392, filed on Feb. 12, 1999, now abandoned, which is a continuation of application No. 08/718,565, filed as application No. PCT/US96/12661 on Aug. 2, 1996, now abandoned.

(60) Provisional application No. 60/001,792, filed on Aug. 2, 1995, and provisional application No. 60/010,982, filed on Feb. 1, 1996.

(51) Int. Cl.$^7$ .................. A61K 31/41; C07D 487/00; C07D 487/02; C07D 413/00; A61P 9/08

(52) U.S. Cl. .................. 514/381; 514/406; 514/231.5; 514/252.13; 514/256; 548/250; 548/364.1; 548/364.4; 548/377.1; 544/111; 544/333; 544/366

(58) Field of Search ................. 514/381, 406, 514/231.5, 252.13, 256; 548/250, 364.1, 364.4, 377.1; 544/111, 333, 366

(56) References Cited

U.S. PATENT DOCUMENTS

| 3,703,513 A | | 11/1972 | Yamamoto et al. | 260/240 |
|---|---|---|---|---|
| 4,965,282 A | | 10/1990 | Takamura et al. | 514/406 |
| 6,022,886 A | * | 2/2000 | Elliott | 514/406 |

FOREIGN PATENT DOCUMENTS

| EP | 0 714 897 A1 | 6/1996 |
|---|---|---|
| WO | WO94/22830 | 10/1994 |

* cited by examiner

*Primary Examiner*—Mukund J. Shah
*Assistant Examiner*—Tamthom N. Truong
(74) *Attorney, Agent, or Firm*—Linda E. Hall; Stephen A. Venetianer; Charles M. Kinzig

(57) ABSTRACT

Novel pyrroles, pyrazoles and triazoles, pharmaceutical compositions containing these compounds and their use as endothelin receptor antagonists as described.

16 Claims, No Drawings

ENDOTHELIN RECEPTOR ANTAGONISTS

This is a continuation of application Ser. No. 09/249,392 filed Feb. 12, 1999; now abandoned which is a continuation of application Ser. No. 08/718,565 filed Feb. 2, 1998; now abandoned which is a 371 of International Application No. PCT/US96/12661, filled Aug. 2, 1996, which claims benefit from the following provisional applications: 60/001,792, filed Aug. 2, 1995 and 60/010,982, filed Feb. 1, 1996.

FIELD OF INVENTION

The present invention relates to novel pyrroles, pyrazoles and triazoles, pharmaceutical compositions containing these compounds and their use as endothelin receptor antagonists.

Endothelin (ET) is a highly potent vasoconstrictor peptide synthesized and released by the vascular endothelium, Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408-C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al, Supra, p. 112.

Endothelin has been associated with the induction of hemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, February, 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int; 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio. 40 (1991) 215–220; Schiff et al., Am. J. Ostet. Gynecol. February 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc. 1991, H1078-H1085. Endothelin also mediates a potent contraction of human prostatic smooth muscle, Langenstroer et al., J. Urology, Vol. 149, p. 495–499.

Thus, endothelin receptor antagonists would offer a unique approach toward the pharmacotherapy of hypertension, acute and chronic renal failure, ischemia induced renal failure, sepsis-endotoxin induced renal failure, prophylaxis and/or treatment of radio-contrast induced renal failure, acute and chronic cyclosporin induced renal failure, cerebrovascular disease, cerebrovascular spasm, subarachnoid hemorrhage, myocardial ischemia, angina, congestive heart failure, acute coronary syndrome, myocardial salvage, unstable angina, asthma, primary pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, diabetic retinopathy, retinopathy, diabetic nephropathy, diabetic macrovascular disease, atherosclerosis, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, subarachnoid hemorrhage, cerebrovascular vasospasm, myocardial ischemia, angina, congestive heart failure, atherosclerosis, diabetic nephropathy, diabetic retinopathy, retinopathy, diabetic macrovascular disease, atherosclerosis and as an adjunct in angioplasty for prevention of restenosis.

This invention further constitutes a method for antagonizing endothelin receptors in an animal, including humans, which comprises administering to an animal in need thereof an effective amount of a compound of Formula (I).

This invention also constitutes intermediates represented by Formula (II). In a further aspect the present invention provides a process for the preparation of a compound of Formula (I)(d).

DETAILED DESCRIPTION OF THE INVENTION

The compounds of this invention are represented by structural Formula (I):

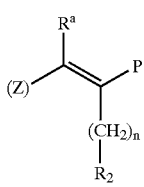

(I)

wherein (Z) is

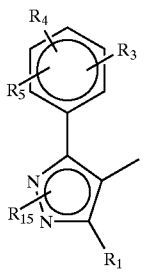

(d)

-continued

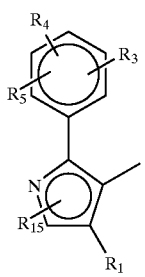

(e)

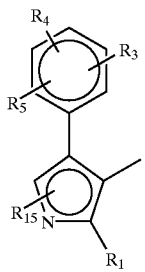

(f)

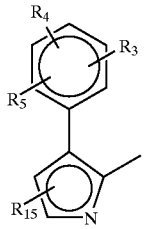

(g)

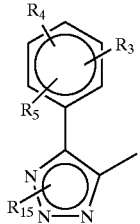

(h)

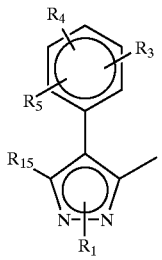

(i)

or

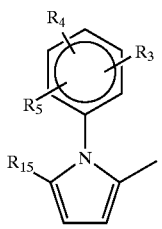

(j)

P is tetrazol-5-yl, $CO_2R_6$ or $C(O)N(R_6)S(O)_qR_{10}$;

$R^a$ is independently hydrogen or $C_{1-6}$alkyl;

$R_1$ is independently hydrogen, Ar, $C_{1-6}$alkyl or $C_{1-6}$alkoxy;

$R_2$ is Ar, $C_{1-8}$alkyl, $C(O)R_{14}$ or

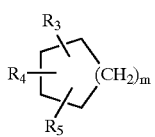

(c)

$R_3$ and $R_5$ are independently $R_{13}OH$, $C_{1-8}$alkoxy, $S(O)_q R_{11} N(R_6)_2$, $NO_2$, Br, F, I, Cl, $CF_3$, $NHCOR_6$, $R_{13}CO_2R_7$, —X—$R_9$—Y, —X$(C(R_6)_2)OR_6$, —$(CH_2)_m X'R_8$ or —$X(CH_2)_n R_8$ wherein each methylene group within —$X(CH_2)_n R_8$ may be unsubstituted or substituted by one or two —$(CH_2)_n$Ar groups;

$R_4$ is independently $R_{11}$, OH, $C_{1-5}$alkoxy, $S(O)_q R_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_n$Ar;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_m C(O)N(R_6)_2$, $C(R_{11})_2 N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or two OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently hydrogen, Ar, $C_{1-6}$alkyl, or XAr;

$R_{16}$ is independently $C_{1-6}$alkyl or phenyl substituted by one or two $C_{1-6}$alkyl, OH, $C_{1-5}$alkoxy, $S(O)_q R_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_n$Ar;

Ar is:

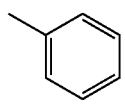

(a)

-continued

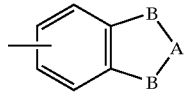

(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or two $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $(CH_2)_q CO_2R_6$, $C(O)N(R_6)_2$, CN, $(CH_2)_n OH$, $NO_2$, F, Cl, Br, I, $N(R_6)_2$, $NHC(O)R_6$, $O(CH_2)_m C(O)NR_a SO_2R_{16}$, $(CH_2)_m OC(O)NR_a SO_2R_{16}$, $O(CH_2)_m NR_a C(O)NR_a SO_2R_{16}$ or tetrazolyl which may be substituted or unsubstituted by one or two $C_{1-6}$alkyl, $CF_3$ or $C(O)R_6$;

m is independently 1 to 3;

n is independently 0 to 6;

q is independently 0, 1 or 2;

provided $R_3$, $R_4$ and $R_5$ are not O—$O(CH_2)_n$Ar; or —O—O—$R_6$;

and further provided that $R_2$ is not dihydrobenzofuran; or a pharmaceutically acceptable salt thereof.

All alkyl, alkenyl, alkynyl and alkoxy groups may be straight or branched.

Halogen may be Br, Cl, F or I.

The compounds of the present invention may contain one or more asymmetric carbon atoms and may exist in racemic and optically active form. All of these compounds and diastereoisomers are contemplated to be within the scope of the present invention.

Preferred compounds are those wherein:

P is $CO_2R_6$; more preferably P is $CO_2H$.

$R_1$ is hydrogen.

$R_2$ is Ar, cyclohexyl or $C_{1-4}$alkyl. More preferably $R_2$ is a group Ar wherein Ar is a group (a) or (b). In said group (a) or (b) $Z_1$ and $Z_2$ are independently hydrogen, $CO_2R_6$, $(CH_2)_n OH$, $C_{1-4}$alkyl or $C_{1-6}$ alkoxy, e.g. methoxy; A is preferably $CH_2$, both Bs are preferably O.

$R_3$ and $R_5$ are independently hydrogen, $CO_2R_6$, OH, $C_{1-8}$alkoxy, $C_{1-8}$alkyl, $N(R_6)_2$, $NO_2$, Br, F, Cl, I, $R_{13}CO_2R_7$, $X(CH_2)_n R_8$, $(CH_2)_m X'R_8$, or $X(C(R_6)_2)_m OR_6$;

In the context of the group $R_3$ and $R_5$ preferably do not represent hydrogen. In particular in the group $R_3$ preferably represents Br, Cl, $C_{1-8}$alkoxy e.g. methoxy; $X(CH_2)_n R_8$, wherein X preferably represents O, n is 0, 1, or 2, and $R_8$ is preferably selected from:

$CO_2R_6$ wherein $R_6$ is preferably hydrogen;

$OR_6$ wherein $R_6$ is preferably H;

tetrazolyl optionally substituted by $C_{1-8}$alkyl e.g. ethyl;

$CONR_7SO_2R_{11}$ wherein $R_7$ is H or $C_{1-8}$alkyl e.g. methyl, $R_{11}$ preferably is $C_{1-8}$alkyl (e.g. methyl, isopryl, or t-butyl) or phenyl optionally substituted by Br, Cl, F, $C_{1-8}$alkyl e.g. methyl;

or $R_8$ is phenyl or pyridyl substituted by one or more Br, Cl, $CO_2H$, $CH_2OH$.

$R_5$ is $C_{1-8}$alkoxy e.g. methoxy, or $N(R_6)_2$ wherein $R_6$ preferably is H or methyl.

$R_4$ is hydrogen, OH, $C_{1-5}$alkoxy, $N(R_6)_2$, Br, F, Cl, I, NHCOCH$_3$, or $S(O)_qC_{1-5}$alkyl wherein the $C_{1-5}$alkyl may be unsubstituted or substituted by OH, methoxy or halogen. $R_4$ is more preferably hydrogen;

$R_6$ is hydrogen or $C_{1-8}$alkyl e.g. methyl and ethyl;

$R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_nAr$. When $R_7$ is $(CH_2)_nAr$, n is preferably zero or 1 and Ar is preferably phenyl substituted or unsubstituted by halogen or $C_{1-5}$ alkoxy.

$R_{11}$ is hydrogen, phenyl, pyridyl wherein the phenyl and pyridyl may be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, CH$_2$OH, $N(R_6)_2$, or halogen;

$R_{12}$ is hydrogen or $C_{1-6}$alkyl.

$R_{13}$ is phenyl, pyridyl, or $C_{2-10}$alkylene, all of which may be unsubstituted or substituted by one or more $CO_2R_6$, OH, CH$_2$OH, $N(R_6)_2$, or halogen;

$R_{15}$ is preferably hydrogen or $C_{1-6}$alkyl e.g. ethyl, isopropyl, n-butyl, cyclopropylmethyl or cyclopropylethyl.

(Z) is preferrably (d).

Preferred compounds are:

(E)-alpha-[[1-Butyl-5-[2-[(2-carboxyphenyl)methoxy]-4-methoxyphenyl]-1H-pyrazol-4-yl]methylene]-6-methoxy-1,3-benzodioxole-5-propanoic acid;

(E)-alpha-[[5-[2-[(2-Carboxyphenyl)methoxy]-4-methoxyphenyl]-1-ethyl-1H-pyrazol-4-yl]methylene]-6-methoxy-1,3-benzodioxole-5-propanoic acid;

(E)-alpha-[[1-Allyl-5-[2-[(2-carboxyphenyl)methoxy]-4-methoxyphenyl]-1H-pyrazol-4-yl]methylene]-6-methoxy-1,3-benzodioxole-5-propanoic acid;

(E)-alpha-[[1-Butyl-5-[2-[(2-carboxyphenyl)methoxy)-4-chlorophenyl]-1H-pyrazol-4-yl]methylene]-6-methoxy-1,3-benzodioxole-5-propanoic acid;

(E)-alpha-[[1-Butyl-5-[4-methoxy-2-[[N-(phenylsulfonyl)]carboxamidomethoxy]phenyl]-1H-pyrazol-4-yl]methylene]-6-methoxy-1,3-benzodioxole-5-propanoic acid;

(E)-3-[1-Butyl-5-[2-[2-carboxyphenyl)methoxy]-4-methoxyphenyl]-1H-pyrazol-4yl]-2-[(2,5-dimethoxyphenyl)methyl]-prop-2-enoic acid;

(E)-alpha-[[1-Butyl-5-[2-[(2-hydroxymethylphenyl)methoxy-4-methoxyphenyl]-1H-pyrazol-4-yl]methylene]-6-methoxy-1,3-benzodioxole-5-propanoic acid;

(E)-alpha-[[1-Butyl-5-[2-[(2-carboxyphenyl)methoxy]-4-methoxyphenyl]-1H-pyrazol-4-yl]methylene]-7-methoxy-1,4-benzodioxan-6-propanoic acid;

(E)-alpha-[[5-[2-[(2-Carboxyphenyl)methoxy]-4-methoxyphenyl]-1-cyclopropylmethyl-1H-pyrazol-4-yl]methylene]-6-methoxy-1,3-benzodioxole-5-propanoic acid;

(E)-alpha-[[1-(3-Butenyl)-5-[2-[(2-hydroxymethylphenyl)methoxy]-4-methoxyphenyl]-1H-pyrazol-4-yl]methylene]-6-methoxy-1,3-benzodioxole-5-propanoic acid;

(E)-alpha-[[5-[2-[(2-Carboxyphenyl)methoxy]-4-methoxyphenyl]-1-cyclopropylethyl-1H-pyrazol-4-yl]methylene]-6-methoxy-1,3-benzodioxole-5-propanoic acid;

(E)-alpha-[[1-Butyl-5-[2-[(2-carboxyphenoxy]methyl)-4-methoxyphenyl]-1H-pyrazol-4-yl]methylene]-6-methoxy-1,3-benzodioxole-5-propanoic acid.

The present invention provides compounds of Formula (I), which may be made by methods similar to those given below.

Compounds of the Formula (Id)

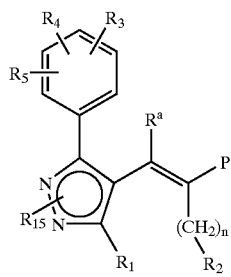

(Id)

can be prepared by alkylating a ketone of Formula (2)

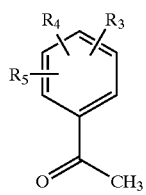

(2)

in dimethyl carbonate in the presence of sodium hydride to provide a β-keto ester of Formula (3).

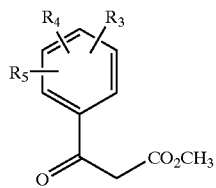

(3)

Condensation of a β-keto ester of Formula (3) with dimethyl formate dimethyl acetal in a suitable solvent such as toluene at approximately 95° C. affords a compound of Formula (4).

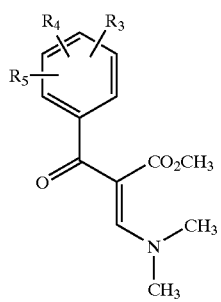

(4)

Treatment of a compound of Formula (4) with a hydrazine derivative of the Formula (5)

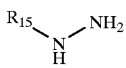 (5)

wherein $R_{15}$ is $C_{1-6}$alkyl;

in suitable solvents such as methanol and water in the presence of sodium acetate provides a pyrazole of Formula (6).

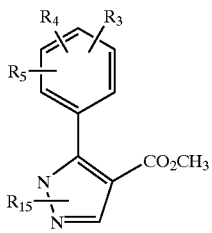 (6)

Reduction of an ester of Formula (6) with a reducing agent such as diisobutylalluminum hydride in a solvent such as dichloromethane followed by oxidation with an oxidant such as Jones reagent in acetone affords an aldehyde of Formula (7).

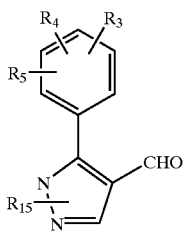 (7)

Knoevenagel condensation of an aldehyde of Formula (7) with a half acid of Formula (8), wherein $R_{16}$ is $C_{1-8}$ alkyl

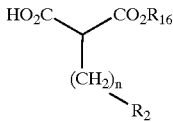 (8)

in a solvent such as benzene at reflux, in the presence of piperidinium acetate with azeotropic removal of water using a Dean-Stark apparatus to afford an ester of Formula (9).

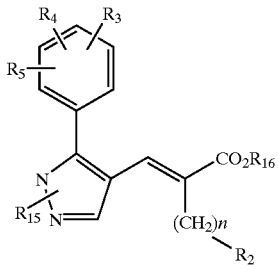 (9)

Followed if necessary and desired by:
1) deprotection and alkylation and hydrolysis of the $R_3$, $R_4$, $R_5$, $R_{15}$, $R_{16}$, $Z_1$ and $Z_2$ groups as required and;
2) salt formation.

Aldehyde condensation may also be effectuated by heating in the presence of pyridine and acetic acid.

Conversion of an ester of formula (9) into an acid may be carried out using conventional deprotection techniques and hydrolysis.

A half acid of Formula (8),

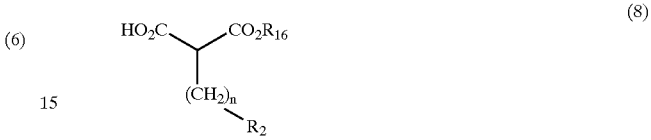 (8)

Wherein n=1, $R_2$ is (b), $A=CH_2$, $B=O$ and $R_{16}$ is $C_{1-6}$ alkyl, may be prepared by reacting a compound of Formula (10)

 (10)

with methyl iodide in the presence of sodium hydride in a solvent such as dimethyl formamide to provide a compound of Formula (11).

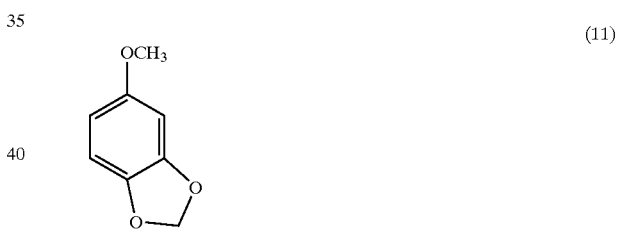 (11)

Treament of a compound of Formula (11) with $POCl_3$ in dimethyl formamide affords an aldehyde of Formula (12).

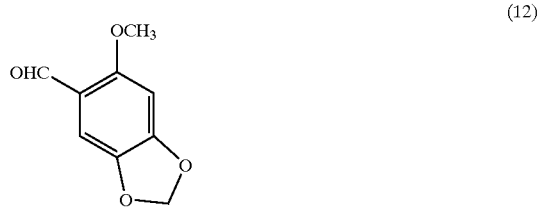 (12)

Condensation of an aldehyde of Formula (12) with a dialkyl malonate of Formula (13)

 (13)

in the presence of piperidine and acetic acid in benzene provides a α,β-unsatuated ester of Formula (14).

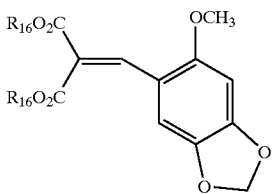

(14)

Reduction of a α,β-unsatuated ester of Formula (14) with sodium borohydride in a solvent such as ethanol gives a compound of Formula of (15)

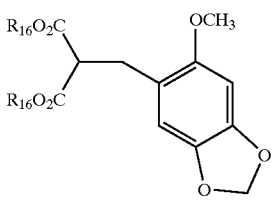

(15)

Monosaponification of a diester of Formula (15) with a base such as potasium hydroxide in a mixture of ethanol and water followed by acidic work up provides a half acid of Formula (8).

Other compounds of formula (Id) may be prepared by methods well known in the art. The invention also is a process for preparing compounds of Formula (Id) by:

(a) Reaction of a compound of Formula (II)

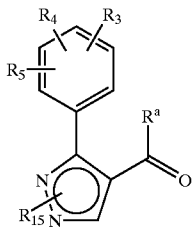

(II)

or a protected form or precursor thereof (as defined hereinafter) with a compound of Formula (8)

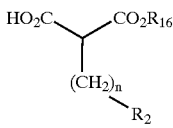

(8)

(wherein $R_2$ and $R_{16}$ are as defined for Formula (Id) hereinabove);

followed if necessary or desired by:

(b) conversion of one compound of Formula (Id) into a different compound of Formula (Id) e.g.
   (i) when Formula (Id) contains a group $CO_2R_6$, $CO_2R_7$ or $CO_2R_{12}$ wherein $R_6$, $R_7$ or $R_{12}$ is alkyl, conversion to a corresponding compound where $R_6$, $R_7$ or $R_{12}$ represents hydrogen;
   (ii) when Formula (Id) contains a hydroxy group (e.g. in $R_3$, $R_4$ or $R_5$) conversion to a different group, e.g.

a group $(CH_2)Ar$ where Ar is optionally substituted phenyl, by method well known in the art; and/or (c) salt formation.

It will be appreciated by those skilled in the art that the substitutents $R_3$, $R_4$, $R_5$, $R_{15}$ and $Z_1$ and $Z_2$ may be introduced at any appropriate stage of the synthesis, preferably at an early stage, using methods well known in the art. In some of the reactions depicted above, particularly those in the early stages of the overall synthesis, one or more of the substitutents may therefore represent a precursor for the eventual substituent. A precursor for any of the substitutents means a group which may be derivatised or converted into the desired group. It will be further appreciated that it may be necessary or desirable to protect certain of these substitutents(or their precursors) at various stages in the reaction sequence. Suitable precursors and protecting groups are well known to those skilled in the art, as are methods for their conversion or removal respectively.

In another aspect the invention provides for an intermediate of the formula (II) wherein $R_{15}$, $R_3$, $R_4$, $R_5$ and $R^a$ are as described for Formula (I)

Compounds of Formula (Ii)

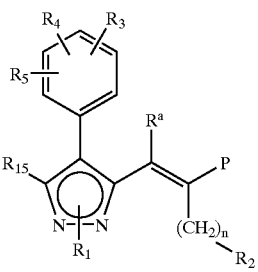

(Ii)

can be prepared starting by commercially available ketones of Formula (17)

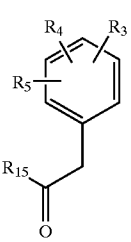

(17)

by reaction with diethyl oxalate of Formula (18)

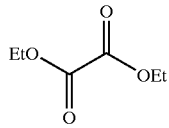

(18)

in the presence of a base such as sodium ethoxide in a solvent such as ethanol to produce a diketone of Formula (19).

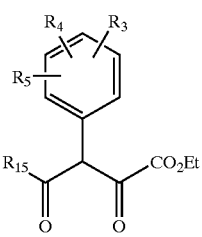
(19)

Reaction of a diketone of Formula (19) with hydrazine derivative of Formula (20)

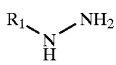
(20)

in a suitable solvent such as ethanol at reflux provides a pyrazole of Formula (21).

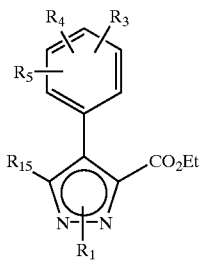
(21)

Saponification of an ester of Formula (21) using lithium hydroxide in a solvent such as aqueous methanol affords, after acidification an acid of the Formula (22),

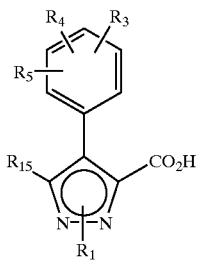
(22)

which can be subsequently converted to the corresponding N-methoxy-N-methylamide of Formula (23)

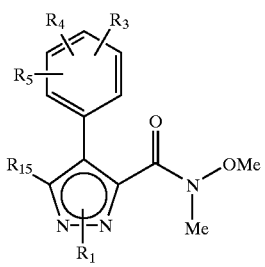
(23)

by treatment with methyl chloroformate followed by N,O-dimethylhydroxylamine hydrochloride in the presence of a base such as N-methylpiperidine. Compound of Formula (23) can be treated with an organometallic reagent Ra—M wherein Ra is $C_{1-6}$ alkyl and m is Li or MgCl; to provide a compound of Formula (24), wherein $R^a$ is $C_{1-6}$alkyl.

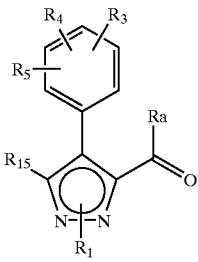
(24)

Reaction of compound of Formula (24) with the the lithium enolate of an ester of Formula (25)

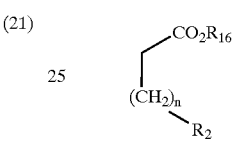
(25)

provides an alcohol of Formula (26)

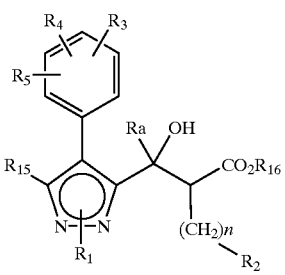
(26)

Dehydration of compound of Formula (26) with acetic anhydride followed by treatment with a base such as 1,8-diazabicyclo[5.4.0]undec-7-ene provides a compound of Formula (27)

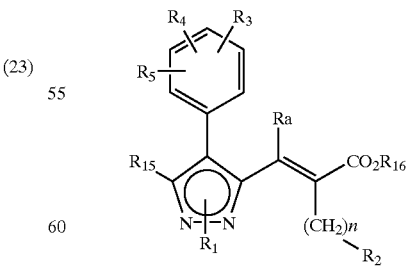
(27)

Alternatively, reaction of compound (24), wherein $R^a$ is $C_{1-6}$alkyl, with Lawesson's reagent in a suitable solvent such as tetrahydrofuran affords a thione of Formula (28),

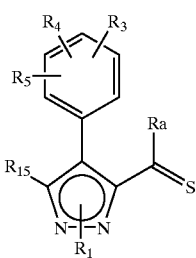

(28)

which can be treated with diazoester (29)

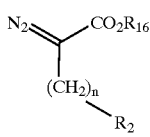

(29)

in refluxing tetrahydrofuran to provide a thiirane of Formula (30).

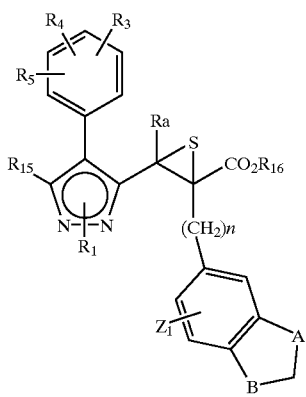

(30)

Treatment of a thiirane of Formula (30) with trimethylphosphite at reflux in a solvent such as chloroform provides compounds of Formula (27), wherein $R^a$ is $C_{1-6}$alkyl.

Saponification of an ester of Formula (27) using lithium hydroxide in a solvent such as aqueous methanol affords, after acidification with acetic acid, an acid of the Formula (Ii), wherein P is $CO_2H$.

Compounds of the Formula (Ie)

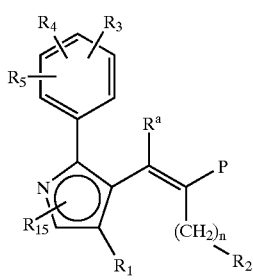

(Ie)

can be prepared following the steps outlined in the following Scheme

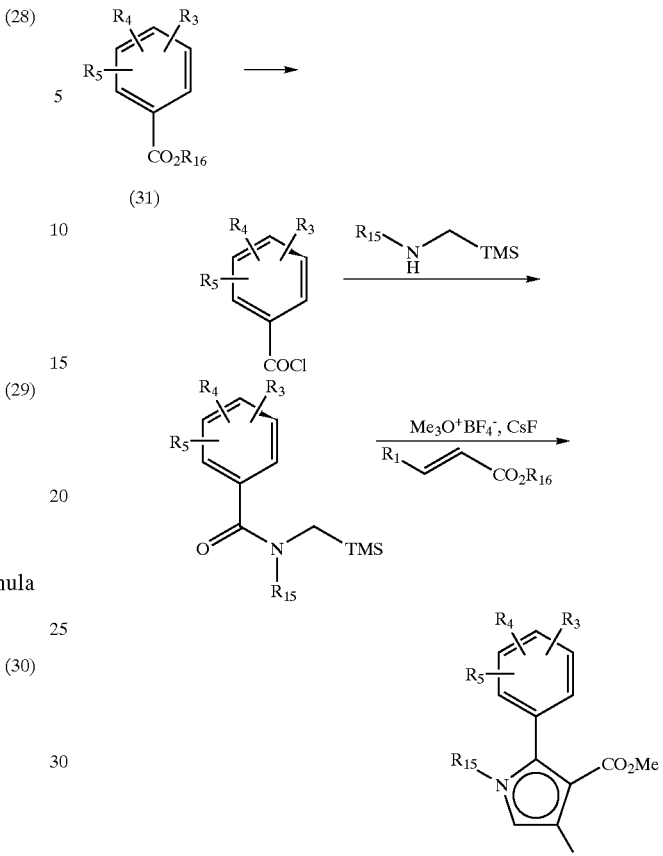

starting from an aryl ester of Formula (31), wherein $R_{16}$ is $C_{1-8}$alkyl, to provide a pyrrole of Formula (32). Compound of Formula (32) can be subsequently converted to compounds of Formula (Ie) following the same sequence of steps as the one described above for the conversions of compound (6) and compound (21) to compounds (Id) and compound (Ii), respectively.

Compounds of Formula (Ih) may be prepared starting from a boronic acid of Formula (33)

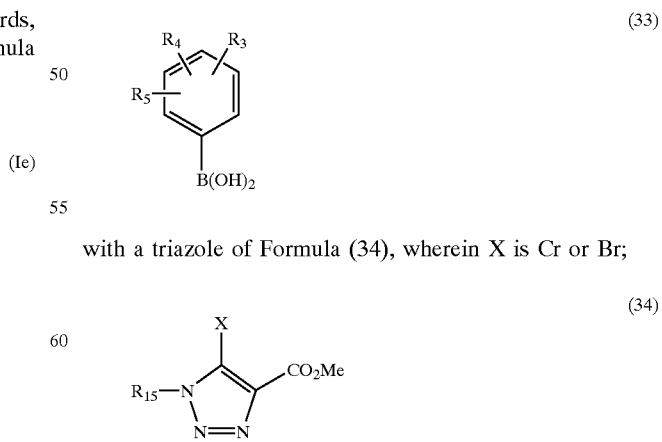

with a triazole of Formula (34), wherein X is Cr or Br;

under standard Suzuki coupling conditions to provide an ester of Formula (35)

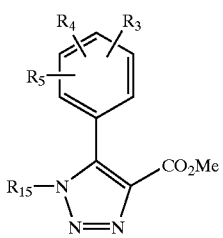
(35)

A compound of Formula (33) may be prepared by reaction of a corresponding organometallic derivative (eg lithium or Grignard) with a trialkyl borate followed by hydrolysis.

A compound of Formula (34) may be prepared starting from dimethyl malonate with p-acetaminobenzenesulfonyl azide in a solvent such as acetonitrile in the of a base such as triethyl amine to provide dimethyl diazomalonate (36).

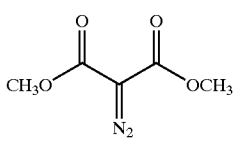
(36)

Treatment of diazomalonate of Formula (36) with an amine of Formula (37)

(37)

followed by acidic work up provides a triazole of Formula (38)

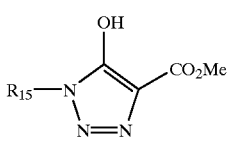
(38)

Reaction of a compound of Formula (38) with $PX_5$, whereas X is Br or Cl, in the presence of potassium carbonate in dimethylformamide affords a compound of Formula (34).

Compounds of Formula (Ij) may be prepared starting from an analine of Formula (39)

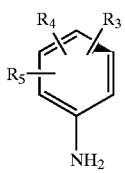
(39)

with a diketone of Formula of (40)

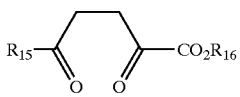
(40)

in a suitable solvent such as ethyl alcohol at reflux to provide a pyrrole of Formula (41).

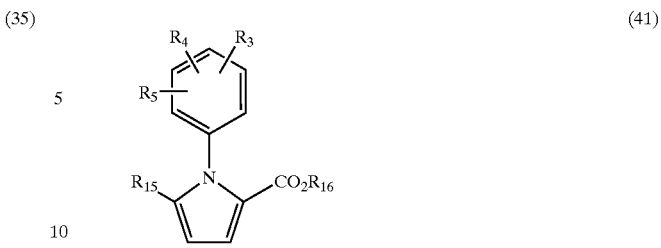
(41)

A diketone of Formula of (40) might be prepared by reacting of α,β-unsatuated ketone of Formula (42)

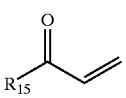
(42)

with a silyl enol ether of Formula (43)

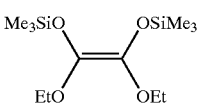
(43)

in the presence of Lewis acid such as zinc chloride in a suitable solvent such as dichloromethane followed by acidic hydrolysis.

Compounds of Formula (35) and compounds of Formula (41) can be subsequently converted to compounds of Formula (Ih) and compounds of Formula (Ij), respectively, following the same sequence of steps as the one described above for the conversions of compound (6), compound (21) and compound (32) to compounds (Id), compound (Ii) and compound (Ie), respectively.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) CHO Cell Membrane Preparation.

CHO cells stably transfected with human $ET_A$ and $ET_B$ receptors were grown in 245 mm×245 mm tissue culture plates in Dulbecco's modified Eagle's medium supplemented with 10% fetal bovine serum. The confluent cells were washed with Dulbecco's phosphate-buffered saline containing a protease inhibitor cocktail (5 mM EDTA, 0.5 mM PMSF, 5 ug/ml of leupeptin and 0.1 U/ml of aprotinin) and scraped in the same buffer. After centrifugation at 800×g, the cells were lysed by freezing in liquid nitrogen and thawing on ice followed by homogenization (30 times using a glass dounce homogenizer) in lysis buffer containing 20 mM Tris HCl, pH 7.5, and the protease inhibitor cocktail. After an initial centrifugation at 800×g for 10 min to remove unbroken cells and nuclei, the supernatants were centrifuged at 40,000×g for 15 min and the pellet was resuspended in 50 mM Tris HCl, pH 7.5, and 10 mM $MgCl_2$ and stored in small aliquots at −70° C after freezing in liquid $N_2$. Protein was determined by using the BCA method and BSA as the standard.

(B) Binding Studies.

$[^{125}I]ET$-1 binding to membranes prepared from CHO cells was performed following the procedure of Elshourbagy et al. (1993). Briefly, the assay was initiated in a 100 ul volume by adding 25 ul of $[^{125}I]ET$-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for $ET_A$ and $ET_B$ receptors, respectively. The incubations (30° C., 60 min) were stopped by dilution with cold buffer (20 mM Tris HCl, pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following examples are illustrative and are not limiting of the compounds of this invention.

EXAMPLE 1

(E)-alpha-[[1-n-Butyl-5-[2-[(2-carboxyphenyl)methoxy]-4-methoxyphenyl]-1H-pyrazol-4-yl]methylene]-6-methoxy-1,3-benzodioxole-5-propanoic Acid a) (E)-Ethyl 6-Methoxy-alpha-[(7-methoxy-4-oxo-4H-1-benzopyran-3-yl)methylene]-1,3-benzodioxole-5-propanoate A solution of 3-formyl-7-methoxychromone (0.67 g, 3.3 mmol) and ethyl hydrogen 2-[(6-methoxy-3,4-methylenedioxy)benzyl]malonate (0.89 g, 3.0 mmol) in benzene (30 mL) was treated with piperidine (0.15 mL, 1.5 mmol) followed by acetic acid (0.085 mL, 1.5 mmol). The reaction was stirred at reflux equipped with a Dean Stark apparatus for 2 h. The mixture was cooled then extracted with EtOAc (200 mL). The organic extract was washed successively with saturated $NaHCO_3$ and brine, dried ($MgSO_4$) and concentrated under vacuum. The resulting residue was purified by column chromatography (silica gel, EtOAc/hexane, gradient 75:25 to 70:30) to afford a material consisting of a 1.2:1 mixture of E:Z enoates as an oil (1.02 g, 78%). Recrystallization of this material from ethanol affords the title compound as the E-isomer, exclusively.

Data for the the E-isomer: mp 140–141° C., MS (ESI) m/z 439 $(M+H)^+$. Anal. Calcd for $C_{24}H_{22}O_8$: C, 65.75; H, 5.06. Found: C, 65.56; H, 4.99.

b) (E)-Ethyl alpha-[[1-Butyl-5-(2-hydroxy-4-methoxyphenyl)-1H-pyrazol-4-yl]methylene]-6-methoxy-1,3-benzodioxole-5-propanoate and (E)-Ethyl alpha-[[1-Butyl-3-(2-hydroxy-4-methoxyphenyl)-1H-pyrazol-4-yl]methylene]-6-methoxy-1,3-benzodioxole-5-propanoate A solution of the compound of Example 1(a) (0.679 g, 1.55 mmol), butylhydrazine oxalate (0.552 g, 3.1 mmol) and sodium acetate trihydrate (1.265 g, 9.3 mmol) in a mixture of 9:1 $EtOH:H_2O$ (31 mL) was stirred at reflux for 1 h. The reaction mixture was cooled and subsequently partitioned between EtOAc (300 mL) and aqueous pH 7 buffer. The organic extract was washed with brine, dried ($Na_2SO_4$) and concentrated under vacuum. The resulting residue was purified by column chromatography (silica gel, EtOAc/hexane, 60:40) to afford the 1,3,4-pyrazole (340 mg, 43%) followed by the isomeric 1,4,5-pyrazole (361 mg, 46%). Data for the 1,4,5-pyrazole: Rf (70:30 hexane:ethyl acetate) 0.14; $^1H$ NMR (400 MHz, $CDCl_3$) δ 0.79 (t, J=7.3Hz, 3H), 1.12–1.21 (m, 2H), 1.20 (t, J=7.2Hz, 3H), 1.67 (quintet, J=7.4 Hz, 2H), 3.79 (s, 3H), 3.83 (s, 3H), 3.86–3.95 (m, 4H), 4.14 (q, J=7.2 Hz, 2H), 5.84 (s, 2H), 6.53 (s, 1H), 6.54 (s, 1H), 6.56 (d, J=2.4 Hz, 1H), 6.61 (dd, J=8.5, 2.4 Hz, 1H), 7.03 (d, J=8.5 Hz, 1H), 7.39 (s, 1H) 7.60 (s, 1H); MS (ESI) m/z 509 $(M+H)^+$.

Data for 1,3,4-pyrazole: Rf(70:30 hexane:ethyl acetate) 0.41; $^1$H NMR (400 MHz, CDCl$_3$) δ 0.91 (t, J=7.3 Hz, 3H), 1.22–1.25 (m, 2H), 1.28 (t, J=7.2 Hz, 3H), 1.80 (quintet, J=7.4 Hz, 2H), 3.76–3.81 (m, 2H), 3.77 (s, 3H), 3.78 (s, 2H), 4.04 (t, J=7.1 Hz, 2H), 4.24 (q, J=7.2 Hz, 2H), 5.88 (s, 2H), 6.49–6.54 (m, 1H), 6.55 (s, 2H), 6.61 (d, J=2.5 Hz, 1H), 7.32 (s, 1H), 7.42 (d, J=8.5 Hz, 1H), 7.92 (s, 1H), 10.5 (s, 1H); MS (ESI) m/z 509 (M+H)$^+$.

c) (E)-Ethyl alpha-[[1-Butyl-5-[4-methoxy-2-[[2-(methoxycarbonyl)phenyl]methoxy]phenyl]-1H-pyrazol-4-yl]methylene]-6-methoxy-1,3-benzodioxole-5-propanoate A solution of the 1,4,5-pyrazole of Example 1(b) (0.34 g, 0.67 mmol) in DMF (2.0 mL) was added dropwise to a slurry of NaH (0.024 g, 1.0 mmol) in DMF (1.3 mL) at room temperature. The reaction was stirred for 3 min at which time was added methyl 2-(bromomethyl)benzoate (0.23 g, 1.0 mmol) and stirring continued for 1 h at room temperature. The mixture was quenched with aqueous pH 7 buffer, then diluted with EtOAc. The organic extract was washed with brine, dried (Na$_2$SO$_4$) and concentrated under vacuum. The resulting residue was purified by column chromatography (silica gel, gradient hexane/Et$_2$O, 60:40 to 50:50) to afford the title compound (396 mg, 90%). Rf (70:30 hexane:ethyl acetate) 0.23; MS (ESI) m/z 657 (M+H)$^+$.

d) (E)-alpha-[[1-Butyl-5-[2-[(2-carboxyphenyl)methoxy]-4-methoxyphenyl]-1H-pyrazol-4-yl]methylene]-6-methoxy-1,3-benzodioxole-5-propanoic Acid To a solution of the ester of Example 1(c) (0.396 g, 0.60 mmol) in MeOH (16.2 mL) was added aqueous LiOH.H$_2$O (0.253 g, 6.0 mmol, in 1.8 mL H$_2$O), and the reaction was heated at reflux for 4 h. After cooling to room temperature, acetic acid (2.5 mL) was added followed by H$_2$O (15 mL) at which time a precipitate formed. Most of the methanol was removed under reduced pressure, and the resulting aqueous solution was cooled to 0° C. The mixture was filtered and the precipitate was recrystallized from EtOAc (−20° C.) to give the title compound as white crystals (0.27 g). The mother liquors were purified by column chromatography (silica gel, gradient CH$_2$Cl$_2$/hexane/EtOAC/HOAc 40:40:20:1 to 40:30:30:1) to afford an additional 86 mg of title compound (356 mg, 96% overall): mp 213–214° C.; Rf(50:50:1 hexane:ethyl acetate: acetic acid) 0.43; $^1$H NMR (400 MHz, CDCl$_3$) δ 0.80 (t, J=7.3 Hz, 3H), 1.21–1.26 (m, 2H), 1.69–1.77 (m, 2H), 3.59 (s, 2H), 3.81 (s, 3H), 3.86 (s, 3H), 3.97–4.02 (m, 2H), 5.53 (s, 2H), 5.82 (s, 2H), 6.47 (s, 1H), 6.52 (s, 1H), 6.67 (dd, J=8.4, 2.2 Hz, 1H), 6.70 (d, J=2.2 Hz, 1H), 7.12 (d J=8.4 Hz, 1H), 7.32–7.36 (m, 2H), 7.48 (t, J=7.6 Hz, 1H), 7.52 (s, 1H), 7.54 (s, 1H), 8.08 (d, J=7.4 Hz, 1H); MS (ESI) m/z 613 (M−H)$^-$. Anal. Calcd for C$_{34}$H$_{34}$N$_2$O$_9$.0.25H$_2$O: C, 65.96; H, 5.62; N, 4.52. Found: C, 65.94; H, 5.44; N, 4.44.

Alternately 1-butyl-5-[2-(2-carboxyphenyl)methoxy]-4-methoxyphenylpyrazole-4-carboxyaldehyde may be prepared as follows.

a) (E)-Methyl 2-[[2-(3-hydroxy-1-oxo-2-propenyl)-5-methoxyphenoxy]methyl]benzoate To a 12 L round bottomed flask, was added 60% sodium hydride (50.9 g, 1.27 mol, 2 equivalents). Toluene (600 mL) was added and the resulting solution was stirred. Methyl 2-[(2-acetyl-5-methoxyphenoxy)methyl]benzoate (200.0 g, 0.636 mol) dissolved in toluene (2.0 L) was added slowly over a period of 20 minutes. After the addition was complete, the solution was stirred for a period of 15 minutes. Methyl formate (229.1 g, 235 mL, 3.82 mol) was added over 20 minutes. The mixture was stirred for 1 hour at ambient temperature. Sodium methoxide (34.3 g, 0.636 mol) was added in three equal portions over 30 minutes. The mixture was stirred at ambient for 16 hours. HPLC of the reaction mixture showed the absence of starting material. Hexane (6 L) was added and the reaction mixture was stirred for 1 hour. The solids were filtered and washed with 2 L of hexane and dried under vacuum (0.5 mTorr) to afford (E)-methyl 2-[[2-(3-hydroxy-1-oxo-2-propenyl)-5-methoxyphenoxy]methyl]benzoate, monosodium salt (303.9 g). The (E)-methyl 2-[[2-(3-hydroxy-1-oxo-2-propenyl)-5-methoxyphenoxy]methyl]benzoate, monosodium salt was slurried in water (3 L) and toluene (4 L) was added. A solution of 10% citric acid (2.5 L) was added and the solution stirred for 1 hour. The layers were separated, and the aqueous layer was extracted with 2 L of toluene. The combined toluene layers were washed with brine solution (2×2 L) and dried (magnesium sulfate), filtered and concentrated to a solid which was triturated with hexane (2 L). The solid was filtered and dried to afford the title compound (188.4 g, 86.6% yield) as a light yellow solid: $^1$H NMR (300 MHz, CDCl$_3$) δ 8.20 (1H, d), 8.05 (1H, d), 7.95 (1H, m), 7.70 (1H, d), 7.65 (1H, m), 7.45 (1H, m), 6.50 (2H, m), 5.65 (2H, m), 5.3 (1H, br s), 3.90 (3H, s), 3.80 (3H, s).

b) (E)-Methyl 2-[[2-[3-(Diethylamino)-1-oxo-2-propenyl]-5-methoxyphenoxy]methyl]benzoate To a 2 L round bottomed flask was added (E)-methyl 2-[[2-(3-hydroxy-1-oxo-2-propenyl)-5-methoxyphenoxy]methyl]benzoate (104 g, 0.304 mol) and 1 L of toluene. After complete dissolution, diethylamine (28.3g, 40 mL, 0.39 mol) was rapidly added under nitrogen via an addition funnel into the stirred solution. The reaction mixture was stirred under nitrogen for 1 h and it was then concentrated under reduced pressure to give approximately 120 g (100% yield) of the title compound as an orange solid: $^1$H NMR (300 MHz, CDCl$_3$) δ 8.02 (1H, d), 7.84 (1H, d), 7.67 (2H, bd), 7.51 (1H, t) 7.35 (1H, t), 6.54 (2H, m), 5.75 (1H, d), 5.52 (2H, s), 3.80 (3H, s), 3.23 (4h, br), 1.14 (6H, br).

c) 1-Butyl-5-[2-(2-methoxycarbonylphenylmethoxy)-4methoxyphenyl]-1H-pyrazole

To a 5 L round bottomed flask was added (E)-methyl 2-[[2-[3-(diethylamino)-1-oxo-2-propenyl]-5-methoxyphenoxy]methyl]benzoate (150 g, 0.37 mol), 2.9 L of methanol and 0.45 L of water. After complete dissolution, a premixed quantity of sodium acetate (294 g, 3.58 mol) and n-butylhydrazine oxalate salt (133 g, 0.746 mol) was added via a powder funnel in rapid portions over a period of 20 minutes. The reaction mixture was blanketed with nitrogen during the reaction period. After 20 hours the reaction mixture was partitioned between 3 L of ethyl acetate and 3 L of water. The aqueous was removed and poured into 2 L of ethyl acetate and the aqueous was separated once again. This operation was repeated once more with 1.2 L of ethyl acetate (a total of 6 L of ethyl acetate used in total). The combined organic extracts were dried (magnesium sulfate) and concentrated under reduced pressure to 187 g of a thick oil. Flash chromatography (50% TBME/Hex) afforded the title compound (153 g, 73% yield) as a colourless oil which slowly solidified on standing: $^1$H NMR (300 MHz, CDCl$_3$) δ 8.02 (1H, d), 7.6 (1H, d), 7.52–7.22 (3H, m), 7.12 (1H, d), 6.64 (1H, d), 6.54 (1H, dd), 6.20 (1H, s), 5.48 (2H, s), 4.01 (2H, t), 3.89 (s 3H), 3.76 (3H, s), 1.7–1.5 (2H, m), 1.2–1.05 (2H, m), 0.7 (3H, t).

d) 1-Butyl-5-[2-(2-methoxycarbonylphenylmethoxy)-4-methoxyphenyl]-1H-pyrazole-4-carboxyaldehyde To a 2 L round bottomed flask was added 235 mL of DMF, followed by phosphorous oxychloride (125.0 g, 75 mL, 0.81 mol) under nitrogen. The temperature of the reaction mixture rose to 40° C. during the addition. The mixture was then allowed to cool to room temperature and then was poured into a separate flask containing 235 mL of DMF and 1-butyl-5-(2-(2-methoxycarbonylphenylmethoxy)-4-methoxyphenyl-1H-pyrazole (145 g, 0.36 mol). The resulting mixture was warmed to 95° C. under nitrogen; it was then allowed to cool and was poured into 1 L of water containing sodium acetate (100 g, 1.13 mol). TBME (1.5 L) was added and the organic phase was separated. An additional 1.5 L of TBME was added. The combined organic phases were dried with magnesium sulfate , filtered and concentrated to 200 g of crude product as a dark oil. Flash chromatography (30% TBME/hexane to 60% hex/TBME) afforded 100 g of solid which was recrystallized (TBME/Hex) to give the title compound (91.3 g, 58% yield) as a white solid: $^1$H NMR (300 MHz, CDCl$_3$) δ 9.54 (1H, s), 8.1 (1H, s), 8.02 (1H, d), 7.45 (1H, t), 7.31 (1H, t), 7.29–7.261 (1H, m), 7.20 (1H, d), 6.71 (1H, s), 6.55 (1H, d), 5.5 (2H, s), 4.0 (2H, t), 3.92 (3H,s), 1.82–1.64 (2H, m), 1.22–1.08 (2H, m), 0.8 (3H, t).

e) 1-Butyl-5-[2-(2-carboxyphenyl)methoxy]-4-methoxyphenylpyrazole-4-carboxyaldehyde To a 2 L round bottomed flask equipped with an air driven stirrer and condenser was added 1-butyl-5-[2-(2-methoxycarbonylphenylmethoxy)-4-methoxyphenyl-1H-pyrazole-4-carboxyaldehyde (92 g, 0.218 mol), 0.883 L of methanol and lithium hydroxide (14.1 g, 0.336 moles, 1.54 eq). The mixture was warmed to 70° C. and 0.222 L of water was added and the resultant light yellow mixture was maintained at 65° C. for 2 hours under nitrogen atmosphere. The solution was allowed to cool and then was concentrated under reduced pressure to give a thick oil. The oil was sequentially treated with citric acid (60 g, 0.285 moles, 1.3 eq) predissolved in 1.0 L of water and 1 L of dichloromethane. The organic layer was removed and the aqueous layer was washed with 0.5 L of dichloromethane. The organic layers were combined, dried (magnesium sulfate), filtered through a pad of celite, and then concentrated under reduced pressure. This oil was redissolved in 0.8 L of toluene and placed in a −20° C. freezer for 12 hours. The solid formed was filtered, washed with 500 mL of toluene and placed in an oven and dried to constant weight (1.0 Torr @ 50° C.) to afford the title compound (72 g, 81% yield) as a white solid: $^1$H NMR (300 MHz, CDCl$_3$) δ 9.55 (1H, s), 8.15–8.10 (2H, m), 7.51 (1H, t), 7.35 (1H, t), 7.28 (1H, d), 7.20 (1H, d), 6.70 (1H, s), 6.52 (1H,dd), 5.51 (2H, s), 4.1–3.90 (2H, m), 3.85 (3H, s), 1.82–1.64 (2H, m), 1.22–1.08 (2H, m), 0.8 (3H, t).

EXAMPLE 2

(E)-alpha-[[1-n-Butyl-3-[2-[(2-carboxyphenyl)methoxy]-4-methoxyphenyl]-1H-pyrazol-4-yl]methylene]-6-methoxy-1,3-benzodioxole-5-propanoic Acid a) (E)-Ethyl alpha-[[1-Butyl-3-[4-methoxy-2-[[2-(methoxycarbonyl)phenyl]methoxy]phenyl]-1H-pyrazol-4yl]methylene]-6-methoxy-1,3-benzodioxole-5-propanoate To a solution of the 1,3,4-pyrazole of Example 1(b) (0.23 g, 0.45 mmol) in DMF (5 mL) was added NaH (0.04 g, 1.83 mmol) at 0° C. The reaction stirred for 3 min at which time was added methyl 2-(bromomethyl)benzoate (0.22 g, 0.80 mmol) and stirring continued for 1.5 h at room temperature. The mixture was partitioned with EtOAc and 2% HCl, the resulting organic layer was then washed with water (2×). The aqueous layer was then neutralized with NaHCO$_3$ to pH 7 and then partitioned with EtOAc. The combined organic extract was washed with brine, dried (MgSO$_4$) and concentrated under vacuum. The resulting residue was purified by column chromatography (silica gel, gradient hexane Et$_2$O, 67:33 to 65:35) to afford the title compound as an oil (0.25 g, 81%). $^1$H NMR (400 MHz, CDCl$_3$) δ 0.91 (t, J=7.4 Hz, 3H), 1.13 (t, J=7.1 Hz, 3H), 1.30 (sextet, J=7.4 Hz, 2H), 1.83 (quintet, J=7.4 Hz, 2H), 3.73 (s, 2H), 3.85 (s, 3H), 3.86 (s, 3H), 3.89 (s, 3H), 4.07 (q, J=7.1 Hz, 2H), 4.08 (t, J=7.4 Hz, 2H), 5.51 (s, 2H), 5.87 (s, 2H), 6.49 (s, 1H), 6.59 (s, 1H), 6.61 (dd, J=8.4, 2.2 Hz, 1H), 6.69 (d, J=2.2Hz, 1H), 7.31 (t, J=7.8Hz, 1H), 7.34 (d, J=8.4 Hz, 1H), 7.39 (s, 1H), 7.46 (t, J=7.7 Hz, 1H), 7.61 (d, J=7.8 Hz, 1H), 7.70 (s, 1H), 7.99 (d, J=7.8 Hz, 1H).

b) (E)-alpha-[[1-Butyl-3-[2-[(2-carboxyphenyl)methoxy]-4-methoxyphenyl]-1H-pyrazol-4-yl]methylene]-6-methoxy-1,3-benzodioxole-5-propanoic Acid To a solution of the ester of example 2(a) (0.21 g, 0.33 mmol) in MeOH (13.5 mL) was added aqueous LiOH (0.13 g, 3.0 mmol, in 1.5 mL H$_2$O), and the reaction was heated at reflux for 5 h. To the mixture was added acetic acid (1 mL) and most of the solvent was removed under reduced pressure. The residue was partitioned between EtOAc and brine. The organic layer was dried (MgSO$_4$) and concentrated under vacuum. The resulting residue was purified by column chromatography (silica gel, CH$_2$Cl$_2$/EtOAc/hexane/HOAc, 40:30:30:1) to give a white solid, which was recrystallized from EtOAc to afford the title compound (0.175 g, 86%): mp 226–227° C.; 1H NMR (400 MHz, CDCl$_3$) δ 0.94 (t, J=7.3 Hz, 3H), 1.33 (sextet, J=7.3 Hz, 2H), 1.85 (quintet, J=7.3 Hz, 2H), 3.44 (s, 2H), 3.82 (s, 3H), 3.85 (s, 3H), 4.10 (t, J=7.2 Hz, 2H), 5.65 (s, 2H), 5.85 (s, 2H), 6.47 (s, 1H), 6.57 (s, 1H), 6.62 (dd, J=8.4, 2.1 Hz, 1H), 6.67 (d, J=2.1 Hz, 1H), 7.32–7.37 (m, 2H), 7.43 (d J=8.4 Hz, 1H), 7.48–7.52 (m, 2H), 7.76 (s, 1H), 8.12 (d, J=7.9 Hz, 1H); MS (ESI) m/z 615 (M+H)$^+$. Anal. Calcd for C$_{34}$H$_{34}$N$_2$O$_9$ .0.25H$_2$O: C, 65.97; H, 5.62; N, 4.52. Found: C, 65.84; H, 5.46; N, 4.31.

EXAMPLE 3

(E)-alpha-[[1-n-Butyl-5-[2-[(2-carboxyphenyl)methoxy]-5-chloro-4-methylphenyl]-1H-pyrazol-4-yl]methylene]-6-methoxy-1,3-benzodioxole-5-propanoic Acid a) (E)-Ethyl 6-Methoxy-alpha-[(6-chloro-7-methyl-4-oxo-4H-1-benzopyran-3-yl)methylene]-1,3-benzodioxole-5-propanoate Following the procedure of Example 1(a), except substituting 6-chloro-3-formyl-7-methylchromone for 3-formyl-7-methoxychromone, the title compound as prepared in 38% yield: mp (hexane/ethyl acetate) 134–135° C.

b) (E)-Ethyl alpha-[[1-Butyl-5-(5chloro-2-hydroxy-4-methylphenyl)-1H-pyrazol-4-yl]methylene]-6-methoxy-1,3-benzodioxole-5-propanoate Following the procedure of Example 1(b), except substituting the compound of Example 3(a) for (E)-ethyl 6-methoxy-alpha-[(7-methoxy-4oxo-4H-1-benzopyran-3-yl)methylene]-1,3-benzodioxole-5-propanoate, the title compound was prepared in 41% yield: MS (ESI) m/z 527 (M+H)$^+$.

c) (E)-Ethyl alpha-[[1-Butyl-5-[5-chloro-2-[[2-(methoxycarbonyl)phenyl]methoxy]-4-methylphenyl]-1H-pyrazol-4-yl]methylene]-6-methoxy-1,3-benzodioxole-5-propanoate Following the procedure of Example 1(c), except substituting the compound of Example 3(b) for (E)-ethyl alpha-[[1-butyl-5-(2-hydroxy-4-methoxyphenyl)-1H-pyrazol-4yl]methylene]-6-methoxy-1,3-benzodioxole-5-propenoate, the title compound was prepared in 90% yield: MS (ESI) m/z 675 (M+H)$^+$.

d) (E)-alpha-[[1-Butyl-5-[2-[(2-carboxyphenyl)methoxy]-5-chloro-4-methylphenyl]-1H-pyrazol-4-yl]methylene]-6-methoxy-1,3-benzodioxole-5-propanoic Acid Following the procedure of Example 1(d), except substituting the compound of Example 3(c) for (E)-ethyl alpha-[[1-butyl-5-[4-methoxy-2-[[2-(methoxycarbonyl)phenyl]methoxy]phenyl]-1H-pyrazol-4-yl]methylene]-6-methoxy-1,3-benzodioxole-5-propanoate, the title compound was prepared in 83% yield. mp 114–116° C.

EXAMPLE 4

(E)-alpha-[[1-n-Butyl-5-[2-[(2-carboxyphenyl)methoxy-4-chlorophenyl]-1H-pyrazol-4-yl]methylene]-6-methoxy-1,3-benzodioxole-5-propanoic Acid 110° C. (dec).

EXAMPLE 5

(Z)-alpha-[[1-n-Butyl-5-[2-[(2-carboxyphenyl)methoxy]-4-methoxyphenyl]-1H-pyrazol-4-yl]methylene]-6-methoxy-1,3-benzodioxole-5-propanoic Acid

188–189° C.

EXAMPLE 6

(E)-alpha-[[1-Hydro-(3-[(2-Carboxyphenyl)methoxy]-4-methoxyphenyl]-1H-pyrazol-4-yl]methylene]-6-methoxy-1,3-benzodioxole-5-propionic Acid

EXAMPLE 7

(E)-alpha-[[1-Ethyl[5-[(2-carboxyphenyl)methoxy]-4-methoxyphenyl]-1H-pyrazol-4-yl]methylene]-6-methoxy-1,3-benzodioxole-5-propionic Acid

EXAMPLE 8

(E)-alpha-[[1-Allyl-[5-(2-carboxyphenyl)methoxy]-4-methoxyphenyl]-1H-pyrazol-4-yl]methylene]-6-methoxy-1,3-benzodioxole-5-propionic Acid

EXAMPLE 9

(E)-alpha-[[1-n-Butyl-5-[2-[(2-carboxyphenyl)methoxy]-4,5-dichlorophenyl]-1H-pyrazol-4-yl]methylene]-6-methoxy-1,3-benzodioxole-5-propanoic Acid

226–228° C.

EXAMPLE 10

(E)-alpha-[[1-n-Butyl-[3-[4-methoxy-2-[[N-(phenylsulfonyl)]carboxamido-methoxy]phenyl]-1H-pyrazol-4-yl]methylene]-6-methoxy-1,3-benzodioxole propionic Acid

EXAMPLE 11

(E)-3-[1-n-Butyl-5-[2-[(2-carboxyphenyl)methoxy]-4-methoxyphenyl]-1H-pyrazol-4-yl]-2-[(3,5-dimethoxyphenyl)methyl]-prop-2-enoic Acid

EXAMPLE 12

(E)-alpha-[[1-n-Butyl-5-[4-methoxy-2-[[N-(phenylsulfonyl)]carboxamido-methoxy]phenyl]-1H-pyrazol-4-yl]methylene]-6-methoxy-1 3-benzodioxole-5-propanoic Acid

EXAMPLE 13

(E)-3-[1-n-Butyl-5-[2-2-carboxyphenyl)methoxy]-4-methoxyphenyl]-1H-pyrazol-4-yl]-2-[(2,3-dimethoxyphenyl)methyl]-prop-2-enoic Acid

188–189° C.

EXAMPLE 14

(E)-3-[1-n-Butyl-5-[2-[2-carboxyphenyl)methoxy]-4methoxyphenyl]-1H-pyrazol-4-yl]-2-[(2,5-dimethoxyphenyl)methyl]-prop-2-enoic Acid

192–194° C.

EXAMPLE 15

(E)-alpha-[[1-Benzyl-5-[2-[(2-carboxyphenyl)methoxy]-4-methoxyphenyl]-1H-pyrazol-4-yl]methylene]-6-methoxy-1,3-benzodioxole-5-propanoic Acid

EXAMPLE 16

(E)-3-[1-n-Butyl-5-[2-[2-carboxyphenyl)methoxy]-4-methoxyphenyl-1H-pyrazol-4-yl-2-[(2,6-dimethoxyphenyl)methyl]-prop-2-enoic Acid

EXAMPLE 17

(E)-3-[1-n-Butyl-5-[2-[2-carboxyphenyl)methoxy]-4-methoxyphenyl]-1H-pyrazol-4-yl]-2-[(2,5-dichlorophenyl)methyl]-prop-2-enoic Acid

177–179° C.

EXAMPLE 18

(E)-alpha-[[1-n-Butyl-5-[2-[(2-hydroxymethylphenyl)methoxy]-4-methoxyphenyl-1H-pyrazol-4-yl]methylene]-6-methoxy-1,3-benzodioxole-5-propanoic Acid

EXAMPLE 19

(E)-alpha-[[1-n-Butyl-5-[2-[(2-carboxyphenyl)methoxy]-4-methoxyphenyl]-1H-pyrazol-4-yl]methylene]-6-methoxy-1,3-benzodioxan-5-propanoic Acid

124–126° C.

EXAMPLE 20

(E)-alpha-[[5-[2-[(2-Carboxyphenyl)methoxy]-4-methoxyphenyl]-1-cyclopropyl-methyl-1H-pyrazol-4-yl]methylene]-6-methoxy-1,3-benzodioxole-5-propanoic Acid

EXAMPLE 21

(E)-3-[1-n-Butyl-5-[2-(2-carboxyphenyl)methoxy]-4-methoxyphenyl]-1H-pyrazol-4-yl-2-[(2-methoxy-5-chlorophenyl)]-prop-2-enoic Acid

202–203° C.

EXAMPLE 22

(E)-3-[1-n-Butyl-5-[2-(2-carboxyphenyl)methoxy]-4-methoxyphenyl]-1H-pyrazol-yl-4-]-2-[2-chloro-5-methoxyphenyl]-prop-2-enoic Acid

141–143° C.

EXAMPLE 23

(E)-alpha-[[1-n-Butyl-5-[2-[(2-Carboxyphenyl)methoxy]-4methoxyphenyl]-1H-pyrazol-4-yl]methylene-2-chloro-5-thiophene propanoic Acid

EXAMPLE 24

(E)-alpha-[[1-n-Butyl]-5-[2-[(2-carboxyphenyl)methoxy]-4-methoxyphenyl-1H-pyrazol-4-yl]methylene-3-indolepropanoic Acid

EXAMPLE 25

(E)-3-[1-n-Butyl-5-[2-[2-(carboxyphenyl)methoxy]-4-methoxyphenyl]-1H-pyrazol-4-yl]-2-[(2,4-dmethoxyphenyl)methyl]-prop-2-enoic Acid

197–199° C.

EXAMPLE 26

(E)-3-[1-n-Butyl-5-[2-(2-carboxyphenyl)methoxy]-4-methoxyphenyl]-1H-pyrazol-4-yl]-2-[(5-fluoro-2-methoxyphenyl)methyl]-prop-2-enoic Acid

200–201° C.

EXAMPLE 27

(E)-3-[1-n-Butyl-5-[2-(2-carboxyphenyl)methoxy]-4-methoxyphenyl]-1H-pyrazol-4-yl]-2-[(2-methoxy-5-nitrophenyl)methyl]-prop-2-enoic Acid

239–241° C.

EXAMPLE 28

(E)-3-[1-n-Butyl-5-[2-(2-carboxyphenyl)methoxy]-4-methoxyphenyl]-1H-pyrazol-4yl]-2-[(2-methoxyphenyl)methyl]-prop-2-enoic Acid

182–183° C.

EXAMPLE 29

(E)-3-[1-n-Butyl-5-[2-(2-carboxyphenyl)methoxy]-4-methoxyphenyl]-1H-pyrazol-4-yl]-2-[5-benzyloxy-2-methoxyphenyl)methyl]-prop-2-enoic Acid

180–183° C.

EXAMPLE 30

(E)-3-[1-n-Butyl-5-[2-(2-carboxyphenyl)methoxy]-4-methoxyphenyl]-1H-pyrazol-4-yl]-2-[(2-methoxyphenyl-5-methylthio)methyl]-prop-2-enoic Acid

158–160° C.

EXAMPLE 31

(E)-alpha-[[1-n-Butyl-5-[2-[(2-carboxyphenyl)methoxy]-4-methoxyphenyl]-1H-pyrazol-4-yl]methylene]-2,4-dibromo-5-methoxybenzenepropanoic Acid

EXAMPLE 32

(E)-alpha-[[1-n-Butyl-5-[2-[(2-carboxyphenyl)methoxy]-4-methoxyphenyl-1H-pyrazol-4-yl]methylene]-4-chloro-2,5-dimethoxybenzenepropanoic Acid

EXAMPLE 33

(E)-alpha-[[1-(3-Butenyl)-5-[2-[(2-carboxyphenyl)methoxy]-4-methoxyphenyl]-1H-pyrazol-4-yl]methylene]-6-methoxy-1,3-benzodioxole-5-propanoic Acid

EXAMPLE 34

(E)-alpha-[[5-[2-[(2-Carboxyphenyl)methoxy]-4-methoxyphenyl]-1-cyclopropyl-ethyl-1H-pyrazol-4-yl]methylene]-6-methoxy-1,3-benzodioxole-5-propanoic Acid

EXAMPLE 35

(E)-alpha-[[1-n-Butyl-5-[2-[N-(phenylsulfonyl)-(N-methyl)methylurea]-4-methoxy-phenyl]-1H-pyrazol-4-yl]-methylene]-6methoxy-1,3-benzodioxan-5-propanoic Acid Trifluoroacetate Salt

58–60° C.

EXAMPLE 36

(E)-alpha-[[1-n-Butyl-5-[2-(2-carboxyphenylmethylether)-4methoxyphenyl]-1H-pyrazol-4-yl]methylene]-6-methoxy-1,3-benzodioxan-5-propanoic Acid

185–187° C.

EXAMPLE 37

(E)-3-[1-n-Butyl-5-[2-(2-carboxyphenyl)methoxy-4-methoxyphenyl]-1,2,3-triazol-4-yl]-2-[(2-methoxy-4,5-methylenedioxy)phenylmethyl]-prop-2-enoic Acid m.p. 195° C.

EXAMPLE 38

(E)-3-[1-n-Butyl-5-[2-(2-hydroxymethyl)phenylmethoxy-4-methoxyphenyl]-1,2,3-triazol-4-yl]-2-[(2-methoxy-4,5-methylenedioxy)phenylmethyl]-prop-2-enoic Acid m.p. 134–137° C.

EXAMPLE 39

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
| --- | --- |
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2,38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

What is claimed is:

1. A compound of Formula (I):

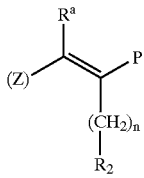

(I)

wherein (Z) is

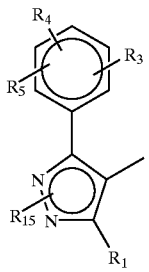

(d)

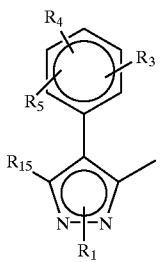

(i)

P is tetrazol-5-yl, $CO_2R_6$ or $C(O)N(R_6)S(O)_qR_{10}$;

$R^a$ is independently hydrogen or $C_{1-6}$alkyl;

$R_1$ is independently hydrogen, Ar, $C_{1-6}$alkyl, or $C_{1-6}$alkoxy;

$R_2$ is Ar, $R_3$ and $R_5$ are independently $R_{13}OH$, $C_{1-8}$alkoxy, $S(O)_qR_{11}$, $N(R_6)_2$, $NO_2$, Br, F, I, Cl, $CF_3$, $NHCOR_6$, $R_{13}CO_2R_7$, —X—$R_9$—Y, —X($C(R_6)_2)_2OR_6$, —$(CH_2)_mX$—$R_8$ or —X$(CH_2)_nR_8$ wherein each methylene group within —X$(CH_2)_nR_8$ may be unsubstituted or substituted by one or two —$(CH_2)_nAr$ groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$ alkyl; or $R_7$ is $(CH_2)_nAr$;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N$ ($R_6)_2$, $C(R_{11})_2N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently hydrogen, Ar, $C_{1-6}$alkyl, or XAr;

$R_{16}$ is independently $C_{1-6}$alkyl or phenyl substituted by one or more $C_{1-6}$alkyl, OH, $C_{1-5}$alkoxy, $S(O)_qR_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_nAr$;

Ar is:

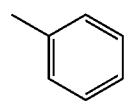

(a)

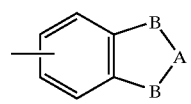

(b)

both of which may be unsubstituted or substituted by one or more $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)$ $NR_aSO_2R_{16}$, $(CH_2)_mOC(O)NR_aSO_2R_{16}$, $O(CH_2)_m$ $NR_aC(O)NR_aSO_2R_{16}$ or tetrazolyl which may be substituted or unsubstituted by $C_{1-6}$alkyl, $CF_3$ or $C(O)R_6$;

m is independently 1 to 3;

n is independently 0 to 6;

q is independently 0, 1 or 2;

provided $R_3$, $R_4$ and $R_5$ are not O—O$(CH_2)_nAr$ or —O—O $R_6$;

and further provided that $R_2$ is not dihydrobenzofuran; or a pharmaceutically acceptable salt thereof.

2. A compound of Formula (I) wherein P is $CO_2R_6$; $R_1$ is hydrogen; $R_2$ is Ar; $R_3$ and $R_5$ are independently hydrogen, $CO_2R_7$, OH, $C_{1-8}$alkoxy, $C_{1-8}$alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_2OR_6$; $R_4$ is hydrogen, OH, $C_{1-5}$alkoxy, $N(R_6)_2$, Br, F, Cl, I, $NHCOCH_3$, or $S(O)_qC_{1-5}$alkyl wherein the $C_{1-5}$alkyl may be unsubstituted or substituted by OH, methoxy or halogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar wherein n is zero or 1 and Ar is substituted phenyl; $R_{11}$ is hydrogen or phenyl, which may be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl or $C_{2-10}$alkylene, both of which may be unsubstituted or substituted by one or more OH, $CH_2OH$, $N(R_6)_2$, or halogen, and the phenyl may be additionally unsubstituted or substituted with $CO_2R_6$; $R_{15}$ is hydrogen or $C_{1-6}$alkyl; and (Z) is (d).

3. A compound of claim 2 wherein P is $CO_2H$; $R_1$ is hydrogen; $R_2$ is a group Ar wherein Ar is a group (a) or (b) and in said group (a) or (b), $Z_1$ and $Z_2$ are independently hydrogen, $CO_2R_6$, $(CH_2)_n$OH, $C_{1-4}$alkyl or $C_{1-6}$ alkoxy and A is $CH_2$, and both Bs are O; $R_3$ is Br, Cl, $C_{1-8}$alkoxy or $X(CH_2)_nR_8$, wherein X is O, n is 0, 1, or 2, and $R_8$ is selected from: $CO_2H$, OH, tetrazolyl optionally substituted by $C_{1-6}$alkyl; $CONR_7SO_2R_{11}$ wherein $R_7$ is H or $C_{1-8}$alkyl, $R_{11}$ is $C_{1-8}$alkyl or phenyl optionally substituted by Br, Cl, F, $C_{1-8}$alkyl; or $R_8$ is phenyl substituted by one or more Br, Cl, $CO_2H$, $CH_2OH$; $R_5$ is methoxy or $N(R_6)_2$ wherein $R_6$ is H or methyl; $R_4$ is hydrogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar wherein $R_7$ is $(CH_2)_n$Ar and n is zero or 1 and Ar is phenyl substituted or unsubstituted by halogen or $C_{1-5}$ alkoxy; $R_{11}$ is hydrogen, phenyl, wherein the phenyl may be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl or $C_{2-10}$alkylene, both of which may be unsubstituted or substituted by one or more OH, $CH_2OH$, $N(R_6)_2$, or halogen, and the phenyl may be additionally unsubstituted or substituted with $CO_2R_6$; $R_{15}$ is hydrogen, ethyl, isopropyl, n-butyl, or cyclopropylethyl; and (Z) is (d).

4. A compound of claim 1 selected from:

(E)-alpha-[[5-[2-[(2-carboxyphenyl)methoxy]-4-methoxyphenyl]-1-ethyl-1H-pyrazol-4-yl]methylene]-6-methoxy-1,3-benzodioxole-5-propanoic acid;

(E)-alpha-[[1-Allyl-5-[2-[(2-carboxyphenyl)methoxy]-4methoxyphenyl]-1H-pyrazol-4-yl]methylene]-6-methoxy-1,3-benzodioxole-5-propanoic acid;

(E)-alpha-[[1-Butyl-5-(2-[(2-carboxyphenyl)methoxy]-4-chlorophenyl]-1H-pyrazol-4-yl]methylene]-6-methoxy-1,3-benzodioxole-5-propanoic acid;

(E)-alpha-[[1-Butyl-5-[4-methoxy-2-[[N-(phenylsulfonyl)]carboxamidomethoxy]phenyl]-1H-pyrazol-4-yl]methylene]-6-methoxy-1,3-benzodioxole-5-propanoic acid;

(E)-3-[1-Butyl-5-[2-[2-carboxyphenyl)methoxy]-4-methoxyphenyl]-1H-pyrazol-4-yl]-2-[(2,5-dimethoxyphenyl)methyl]-prop-2-enoic acid;

(E)-alpha-[[1-Butyl-5-[2-[(2-hydroxymethylphenyl)methoxy]-4-methoxyphenyl]-1H-pyrazol-4-yl]methylene]-6-methoxy-1,3-benzodioxole-5-propanoic acid;

(E)-alpha-[[1-Butyl-5-[2-[(2-carboxyphenyl)methoxy-4-methoxyphenyl]-1H-pyrazol-4-yl]methylene]-7-methoxy-1,4-benzodioxan-6-propanoic acid;

(E)-alpha-[[5-[2-[(2-Carboxyphenyl)methoxy]-4-methoxyphenyl]-1-cyclopropylmethyl-1H-pyrazol-4-yl]methylene]-6-methoxy-1,3-benzodioxole-5-propanoic acid;

(E)-alpha-[[1-(3-Butenyl)-5-[2-[(2-hydroxymethylphenyl)methoxy]-4-methoxyphenyl]-1H-pyrazol-4-yl]methylene]-6-methoxy-1,3-benzodioxole-5-propanoic acid;

(E)-alpha-[[5-[2-[(2-Carboxyphenyl)methoxy]-4-methoxyphenyl]-1H-cyclopropylethyl-1H-pyrazol-4-yl]methylene]-6-methoxy-1,3-benzodioxole-5-propanoic acid;

(E)-alpha-[[1-Butyl-5-[2-[(2-carboxyphenoxy]methyl)-4-methoxyphenyl]-1H-pyrazol-4-yl]methylene]-6-methoxy-1,3-benzodioxole-5-propanoic acid.

5. A compound of claim 1 which is (E)-alpha-[[1-Butyl-5-[2-[(2-carboxyphenyl)methoxy]-4-methoxyphenyl]-1H-pyrazol-4-yl]methylene]-6-methoxy-1,3-benzodioxole-5-propanoic acid.

6. A compound of claim 5 which is the disodium salt thereof.

7. A pharmaceutical composition comprising a compound of claim 1 and a pharmaceutically acceptable carrier.

8. A method of treatment of diseases caused by an excess of endothelin comprising administering to a subject in need thereof, an effective amount of an endothelin receptor antagonist of claim 1.

9. A method of treating renal failure or cerebrovascular disease which comprises administering to a subject in need thereof, an effective amount of a compound of claim 1.

10. A method for the prophylaxis and treatment of radio-contrast induced renal failure which comprises administering to a subject in need thereof, an effective amount of a compound of claim 1.

11. A method of treatment of congestive heart failure which comprises administering to a subject in need thereof, an effective amount of a compound of claim 1.

12. A method of treatment of unstable angina, coronary vasospasm and myocardial salvage which comprises administering to a subject in need thereof, an effective amount of a compound of claim 1.

13. A method of preventing or treating restenosis which comprises administering to a subject in need thereof, an effective amount of a compound of claim 1.

14. A method of treatment of pulmonary hypertension which comprises administering to a subject in need thereof, an effective amount of a compound of claim 1.

15. A method of treatment of stroke or subarachnoid hemorrhage which comprises administering to a subject in need thereof, an effective amount of a compound of claim 1.

16. A process for preparing a compound of Formula (Id) by:

(a) Reaction of a compound of Formula (II)
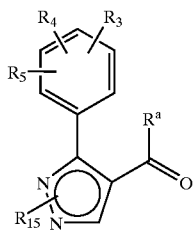
(II)
or a protected form or precursor thereof with a compound of Formula (8)
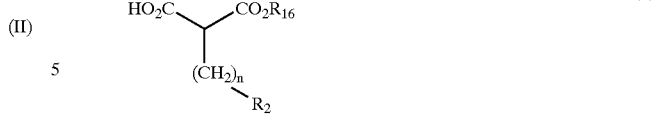
(8)
(wherein $R_2$ and $R_{16}$ are as defined in claim 1 for Formula (Id) hereinabove);
followed if necessary or desired by:
(b) deprotection and alkylation and hydrolysis of the $R_3$, $R_4$, $R_5$, $R_{15}$, $R_{16}$, $Z_1$ and $Z_2$ groups as required and;
(c) salt formation.
* * * * *